United States Patent
Long

(10) Patent No.: US 7,862,583 B2
(45) Date of Patent: Jan. 4, 2011

(54) FUSIBLE SUTURE AND METHOD FOR SUTURING THEREWITH

(75) Inventor: Gary L. Long, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 945 days.

(21) Appl. No.: 10/855,089

(22) Filed: May 27, 2004

(65) Prior Publication Data

US 2005/0277984 A1    Dec. 15, 2005

(51) Int. Cl.
A61B 17/04    (2006.01)

(52) U.S. Cl. ..................................... 606/228

(58) Field of Classification Search .......... 606/228–231
See application file for complete search history.

(56) References Cited

U.S. PATENT DOCUMENTS

| | | | | |
|---|---|---|---|---|
| 3,035,583 A * | 5/1962 | Stoltz et al. | ................... | 606/223 |
| 3,053,124 A * | 9/1962 | Balamuth et al. | ........... | 228/56.2 |
| 3,125,095 A * | 3/1964 | Kaufman | ..................... | 606/226 |
| 3,187,752 A * | 6/1965 | Glick | .......................... | 606/231 |
| 3,513,848 A * | 5/1970 | Garvey et al. | ................ | 606/228 |
| 3,540,452 A * | 11/1970 | Langner et al. | .............. | 606/231 |
| 3,942,532 A * | 3/1976 | Hunter et al. | ................ | 606/231 |
| 4,052,988 A * | 10/1977 | Doddi et al. | ................. | 606/231 |
| 4,185,626 A * | 1/1980 | Jones et al. | .................... | 602/41 |
| 4,662,068 A * | 5/1987 | Polonsky | ...................... | 30/124 |
| 5,127,413 A * | 7/1992 | Ebert | .......................... | 128/898 |
| 5,333,625 A * | 8/1994 | Klein | .......................... | 128/898 |
| 5,569,302 A * | 10/1996 | Proto et al. | ................... | 606/228 |
| 5,893,880 A * | 4/1999 | Egan et al. | .................... | 606/228 |
| 6,077,277 A * | 6/2000 | Mollenauer et al. | ......... | 606/144 |
| 6,174,324 B1 * | 1/2001 | Egan et al. | ................... | 606/232 |
| 6,217,591 B1 * | 4/2001 | Egan et al. | .................... | 606/144 |
| 6,286,746 B1 * | 9/2001 | Egan et al. | .................... | 228/1.1 |
| 6,358,271 B1 * | 3/2002 | Egan et al. | ................... | 606/228 |
| 6,409,743 B1 * | 6/2002 | Fenton, Jr. | ................... | 606/232 |
| 6,432,115 B1 * | 8/2002 | Mollenauer et al. | ......... | 606/148 |
| 6,488,690 B1 * | 12/2002 | Morris et al. | ................ | 606/144 |
| 6,669,705 B2 * | 12/2003 | Westhaver et al. | .......... | 606/139 |
| 6,866,672 B2 * | 3/2005 | Mollenauer et al. | ......... | 606/148 |
| 7,090,111 B2 * | 8/2006 | Egan et al. | .................... | 228/1.1 |

* cited by examiner

*Primary Examiner*—Darwin P Erezo
(74) *Attorney, Agent, or Firm*—Welsh Flaxman & Gitler LLC

(57) ABSTRACT

The present invention relates to a fusible suture for joining portions of tissue. The suture includes an elongate electrical conductor. The conductor extends between opposite ends of the suture and has sufficient flexibility to permit segments of the conductor to overlap, thereby forming a loop sized for joining portions of tissue. The overlapped segments of the conductor are heated upon application of an electrical current to the conductor. The suture further includes a coating that at least partially covers the conductor and extends over at least one of the segments of the conductor. The coating softens when its temperature is at and above a softening temperature so that the overlapping segments of the coating coalesce. The softening temperature is lower than a melting temperature of the conductor. The coating returns to a non-softened state when its temperature falls below a hardening temperature, thereby forming a bond between the overlapped segments of the conductor.

12 Claims, 3 Drawing Sheets

FUSIBLE SUTURE AND METHOD FOR SUTURING THEREWITH

FIELD OF THE INVENTION

The present invention relates to sutures and methods for suturing, and more particularly to fusible sutures and methods for suturing with a fusible suture.

BACKGROUND OF THE INVENTION

Sutures are commonly used to join portions of tissue in a patient. Conventional sutures are made of materials such as silk threads and various mono-filament synthetic materials.

These traditional suture materials require the suture be tied in a knot to join the portions of tissue and secure the suture in place. Tying a knot adds complexity to the surgical process. For example, tying most knots requires control and movement of both ends of the suture. Frequently, loops must be made during knot tying and free ends of the suture are passed through the loops. Thus, surgeons must generally use both hands to tie a knot in a conventional suture. Using both hands is particularly difficult in orthoscopic surgery in which the surgery is performed with specialized instruments through small incisions in the patient to minimize the invasiveness of the surgery. Although complex surgical orthoscopic stapling instruments have been developed to overcome these difficulties, some procedures are best performed using sutures rather than staples. Further, traditional sutures increase the time required for surgery and can become unknotted following surgery, potentially requiring corrective surgery or other intervention. Thus, there is a need for a suture that may be used to join portions of tissue in a patient without tying knots, that may be used during orthoscopic surgery requiring only one incision and instrument, and that may securely join portions of tissue so the suture is unlikely to become untied or otherwise loosen.

BRIEF SUMMARY OF THE INVENTION

The present invention relates to a fusible suture for joining portions of tissue. The suture includes an elongate electrical conductor. The conductor extends between opposite ends of the suture and has sufficient flexibility to permit segments of the conductor to overlap, thereby forming a loop sized for joining portions of tissue. The overlapped segments of the conductor are heated upon application of an electrical current to the conductor. The suture further includes a coating that at least partially covers the conductor and extends over at least one of the segments of the conductor. The coating softens when its temperature is at and above a softening temperature so that the overlapping segments of the coating coalesce. The softening temperature is lower than a melting temperature of the conductor. The coating returns to a non-softened state when its temperature falls below a hardening temperature, thereby forming a bond between the overlapped segments of the conductor.

In another aspect, the present invention includes a method for suturing portions of tissue with a suture having a conductor and a coating surrounding at least a portion of the conductor. The method includes surrounding the portions of the tissue with the suture and overlapping respective segments of the suture. The method further includes fusing the overlapped segments.

Other aspects of the present invention will be in part apparent and in part pointed out hereinafter.

BRIEF DESCRIPTION OF THE FIGURES

Corresponding reference characters indicate corresponding parts throughout the several views of the drawings.

DETAILED DESCRIPTION OF THE INVENTION

Figure 1:
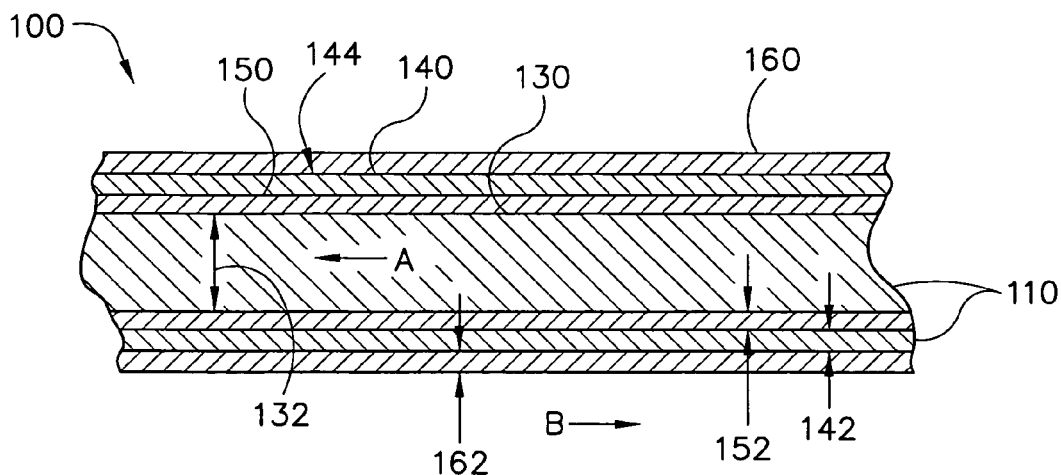
FIG. 1 is a fragmentary side cross section of a first embodiment of a suture according to the present invention.

The present invention relates to a fusible suture and method for suturing with a fusible suture. Referring now to the drawings, and more particularly FIG. 1, a fusible suture according to one embodiment of the present invention is designated in its entirety by the reference number 100. The fusible suture 100 generally includes electrically conductive portion 110 comprising a first, or inner, conductor 130 and a second, or outer, conductor 140. In this embodiment, the conductors 130, 140 are separated by a jacket 150 that is less conductive than the conductive portion 110. The fusible suture 100 further includes a coating 160 formed on an exterior surface of the conductive portion 110. Although the electrical conductors 130, 140 may be made of other materials without departing from the scope of the present invention, in one embodiment the conductors are made of a carbon impregnated thread. In addition, although the first conductor 130 may have other dimensions without departing from the scope of the present invention, in one embodiment the first conductor 130 has a diameter 132 of between about 0.02 millimeters and about 0.5 millimeters. Although the second conductor 140 may have other dimensions without departing from the scope of the present invention, in one embodiment the second conductor 140 has a thickness 142 of between about 0.02 millimeters and about 0.1 millimeters. Further, although the jacket 150 may be made of other materials without departing from the scope of the present invention, in one embodiment the jacket is made of a carbon-based material such as carbon-impregnated polyethylene. Although the jacket 150 may have other dimensions without departing from the scope of the invention, in one embodiment the jacket 150 has a thickness 152 of between about 0.04 millimeters and about 0.2 millimeters. The first and second conductors 130, 140 extend between first and second ends (not shown). The first and second conductors 130, 140 are joined at their respective second ends, such that energy may travel along the first conductor 130 in a first direction A from the first end to the second end along the suture 100 and then return along the second conductor 140 in an opposite direction B. As will be appreciated by those skilled in the art, this configuration allows the suture 100 to be energized and activated from one end (e.g., the first end). In one embodiment the suture 100 has a length of between about 1 meter and about 2 meters or more. Although each conductor 130, 140 is illustrated as being monolithic, it is envisioned the conductors may be made of more than one piece of material (e.g., twisted or braided strands) without departing from the scope of the present invention.

The coating 160 comprises a material that softens and/or melts at a temperature lower than a temperature at which the conductive portion 110 softens and/or melts. For example, the coating may be made of an epoxy that softens at a temperature lower than a temperature at which the conductive portion melts. Although the coating 160 may be made of other materials without departing from the scope of the present invention, in one embodiment the coating is a polyester based hot melt glue, such as HM4165 available from Bostik Findley Incorporated of Middleton, Mass., USA. In one embodiment, the coating 160 has a thickness 162 of between about 0.02 millimeters and about 0.1 millimeters, however, it is envisioned that the coating may have other thicknesses without departing from the scope of the present invention. Further, although the coating 160 is illustrated as covering substantially the entire exterior surface 144 of the conductive portion 110, it is envisioned the coating 160 may extend over less than all of the exterior surface 144 and/or may be interrupted along the exterior surface without departing from the scope of the present invention.

Figure 2:
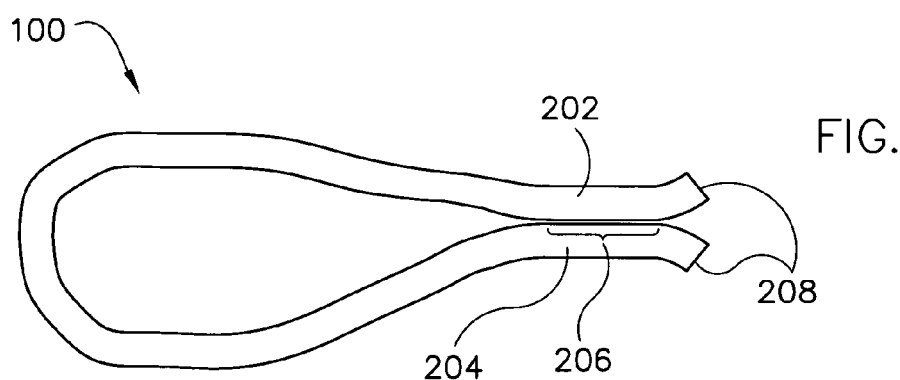
FIG. 2 is a fragmentary elevation of a suture having an overlapped end.
Figure 3:
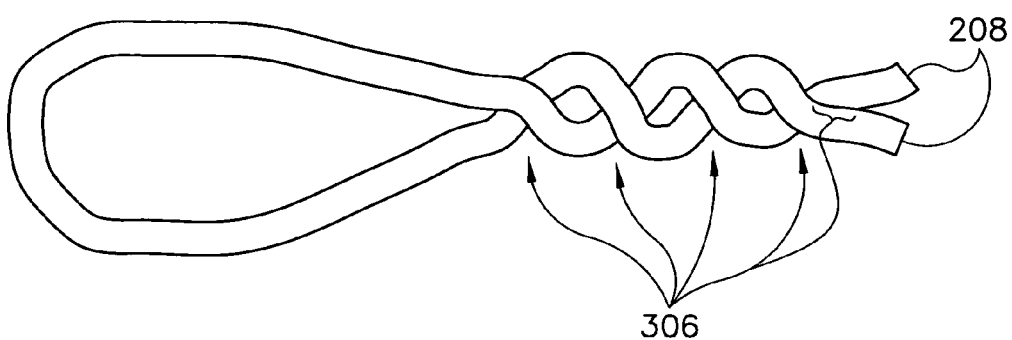
FIG. 3 is a fragmentary elevation of an alternative configuration of a suture having an overlapped end.

The conductive portion 110 and coating 160 are preferably flexible to allow the fusible suture 100 to bend around portions of the tissue to be joined (not shown). The ability to bend allows a user to loop the suture 100 around portions of tissue (not shown) and overlap or cause contact between segments (e.g., segments 202, 204) of the fusible suture 100 as shown in FIG. 2. The overlapped segments of the suture 100 may contact over an extended length 206 as shown in FIG. 2, or at multiple points of contact (generally designated by 306 in FIG. 3) without departing from the scope of the present invention. Further, the overlapping segments of the suture 100 may contact each other in a straight line as shown in FIG. 2 or in spots as shown in FIG. 3 without departing from the scope of the present invention. It will be appreciated that the overlapping segments of the suture 100 may contact in other configurations than shown in FIGS. 2 and 3 (e.g., in a helix) without departing from the scope of the present invention. For instance, it is envisioned the suture 100 may be tied in a knot so segments contact. The suture 100 has opposite ends 208. The overlapping segments and areas of contact may be adjacent these ends 208 or spaced from the ends without departing from the scope of the present invention.

After surrounding the tissue portions and overlapping the portions of the suture 100 so they contact as described above, the coating 160 is activated so it softens and the contacting portions of the coating coalesce. Flow of energy to the suture 100 is stopped so the coating 160 hardens. As the coating 160 hardens, the contacting segments fuse together to maintain the suture 100 in the fused configuration. Because the contacting segments fuse together, the loop surrounding the portions of tissue will be maintained and the suture retains the surrounded portions of tissue so they are joined.

Although the coating 160 may be activated to soften in other ways (e.g., chemically activated), in one embodiment the coating is activated by heating. Although the coating 160 may be heated in other ways without departing from the scope of the present invention, in one embodiment electrical current is passed through the conductive portion 110 to heat the conductive portion, thereby softening the coating 160 and allowing it to coalesce and ultimately fuse when the current is removed and the coating hardens. The jacket 150 at least partially insulates the conductors 130, 140 from each other. In one embodiment the jacket 150 also generates heat in response to activating the conductors 130, 140 which contributes to the activation of the coating 160. Although the electrical current may have other characteristics without departing from the scope of the present invention, in one embodiment the current is a 75 volt, 0.5 amp, direct current supplied by a conventional power source. It is envisioned the supplied current may be alternating current without departing from the scope of the present invention. Once the overlapping portions of the suture 100 are fused, the ends 208 of the suture may be trimmed to a desired length.

Though one suture is illustrated, the present invention is not limited to using only one fusible suture at a time. For example, multiple fusible sutures 100 may be used simultaneously. These sutures may be applied separately or they may be placed in overlapping contact with one another. After overlapping the sutures 100, the conductive portion 110 of each suture is energized, causing the coating 160 corresponding to the points of contact to soften, coalesce and fuse. If a suture 100 needs removal, the suture 100 may be cut using conventional techniques.

Figure 4:
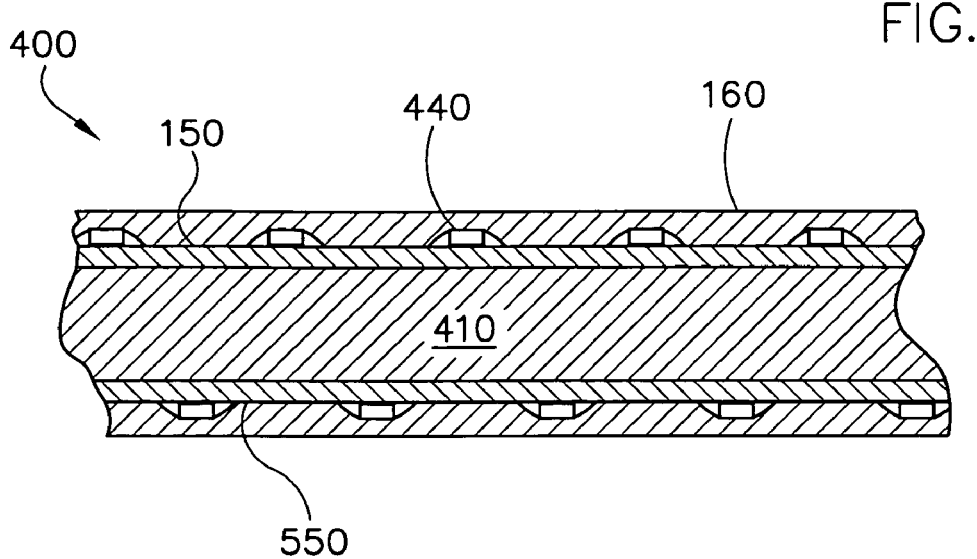
FIG. 4 is a fragmentary side cross section of a second embodiment of a suture according to the present invention.
Figure 5:
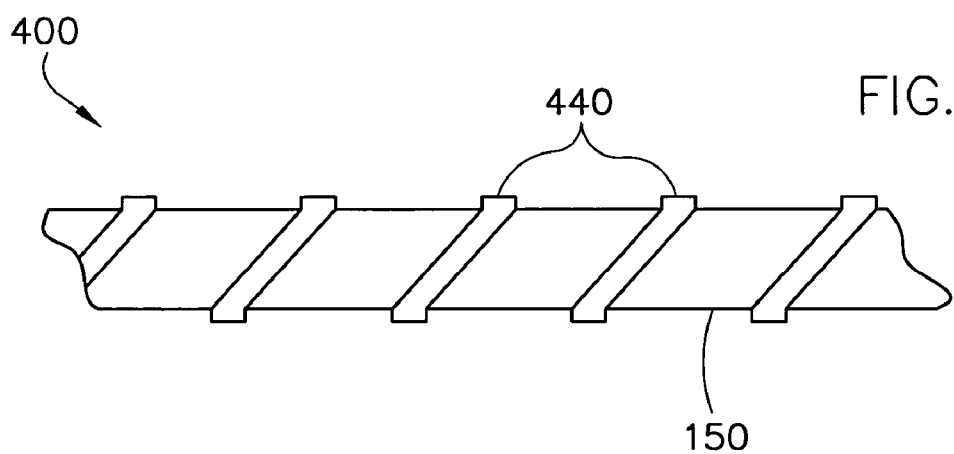
FIG. 5 is a fragmentary elevation of the second embodiment showing a coating removed.
Figure 6:
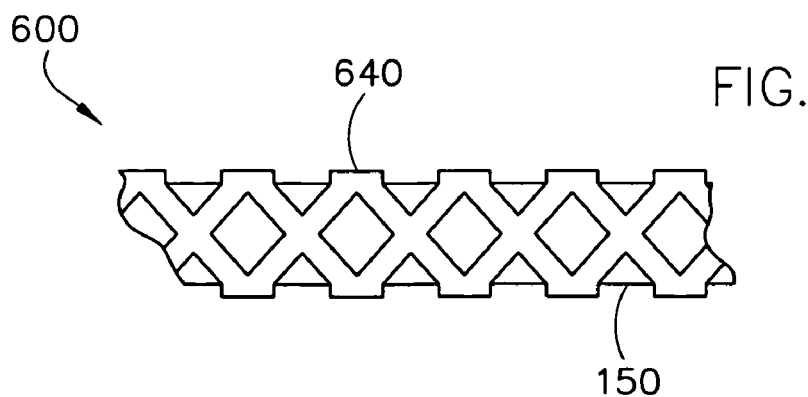
FIG. 6 is a fragmentary of a third embodiment showing the coating removed.

FIG. 4 shows a second embodiment of a suture 400 according to the present invention in which the second conductor 440 of the conductive portion 410 is helically disposed with respect to the jacket 150. Although the coating 160 is shown contacting the jacket 150, the coating may contact the second conductor 440 but be spaced from the jacket 150 without departing from the scope of the present invention. FIG. 5 shows a perspective view of the embodiment of FIG. 4 without the coating 160 to illustrate the manner in which the second conductor 440 may be helically disposed with respect to the jacket 150. Although the second conductor 440 is shown wound around the jacket 150, the second conductor may be disposed around the jacket in other ways without depart from the scope of the present invention. In addition to the manner in which the second conductor 140 is disposed with respect to the jacket 150 in FIG. 1, the second conductor may comprise a plurality of elongate strips (not shown) disposed over the jacket 150. As another example, FIG. 6 shows a third embodiment of a suture 600 according to the present invention in which the second conductor 640 crisscrosses the surface of the jacket 150. The sutures 400, 600 of the second and third embodiments, respectively, are otherwise identical to the suture of the first embodiment, and therefore will not be described in further detail.

Figure 7:
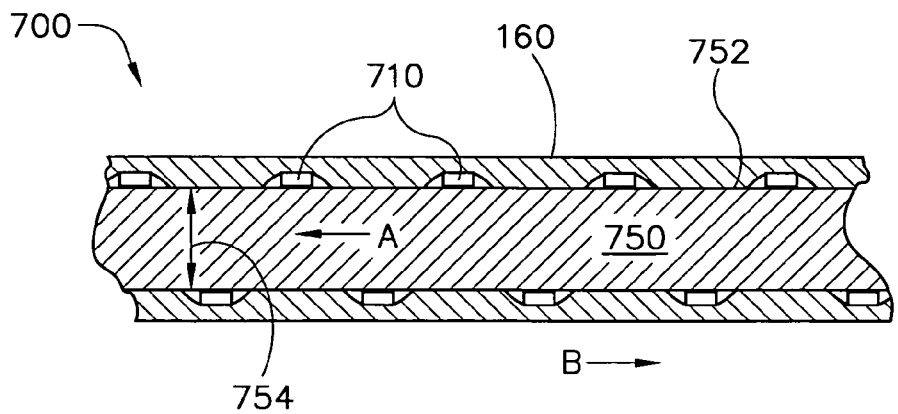
FIG. 7 is a fragmentary side cross section of a fourth embodiment of a suture according to the present invention.
Figure 8:
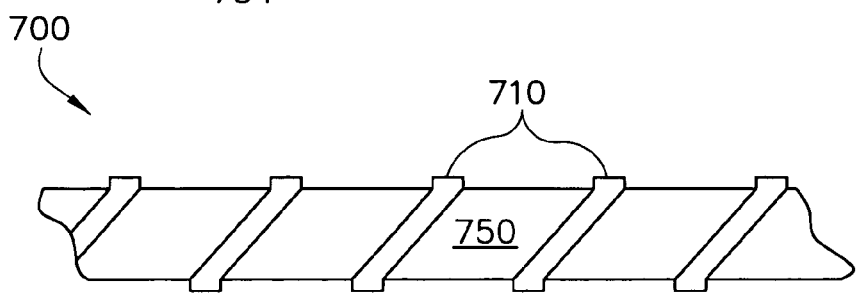
FIG. 8 is a fragmentary elevation of the fourth embodiment showing the coating removed.

FIG. 7 shows a fourth embodiment of a suture 700 according to the present invention in which the fusible suture 700 includes a central core 750. The core 750 is made of a material that is less conductive than the conductors 710. For example, the core may be made of a carbon-based material. The core 750 acts as an insulating or resisting body about which the conductor 110 may be disposed. In one embodiment, in use, the core 750 also generates heat when the conductor 710 is energized. The heat generated by the core 750 contributes to the activation of the coating 160. In the fourth embodiment, one or more conductors 710 are disposed in various ways with respect to the core 750. The one or more conductors 710 are disposed in such a way that energy is able to travel on a first segment of the one or more conductors 710 in a first direction A extending from a first end of the suture (not shown) to an opposite second end (not shown) and return along the suture 700 on a second segment of the one or more conductors 710 in an opposite second direction B. For example, a single conductor 710 may be disposed along the core 750 in two segments connected at the second end (not shown), each extending from the first end to the second end without contacting between the ends. In one configuration, one or more conductors 710 are helically disposed around the exterior surface 752 of the core 750 as shown in FIG. 7. In this embodiment, the one or more conductors 710 may extend from a first end (not shown) of the suture 700 to a second end (not shown) of the suture, and back to the first end without interruption. FIG. 8 illustrates the configuration of FIG. 7 without the coating 160 to show a manner in which the conductors 710 may be wound about the core 750. Although the core 750 may have other diameters without departing from the scope of the present invention, in one embodiment the core has an outer diameter 754 of between about 0.02 millimeters and about 0.5 millimeters. Likewise, although the conductors 710 may have other configurations without departing from the scope of the present invention, in one embodiment the conductors have cross sections that are generally square and have a thickness of between about 0.02 millimeters and about 0.1 millimeters. The suture 700 of the fourth embodiment is otherwise identical to the suture of the first embodiment, and therefore will not be described in further detail.

Figure 9:
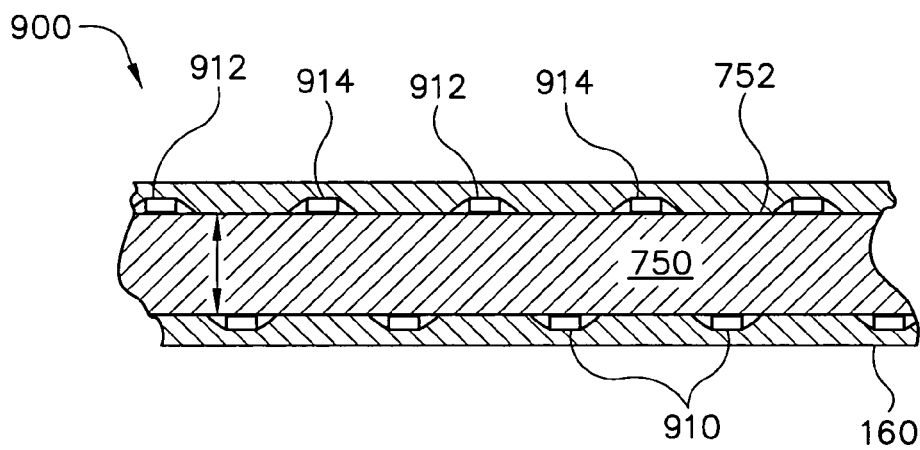
FIG. 9 is a fragmentary side cross section of a fifth embodiment of a suture according to the present invention.
Figure 10:
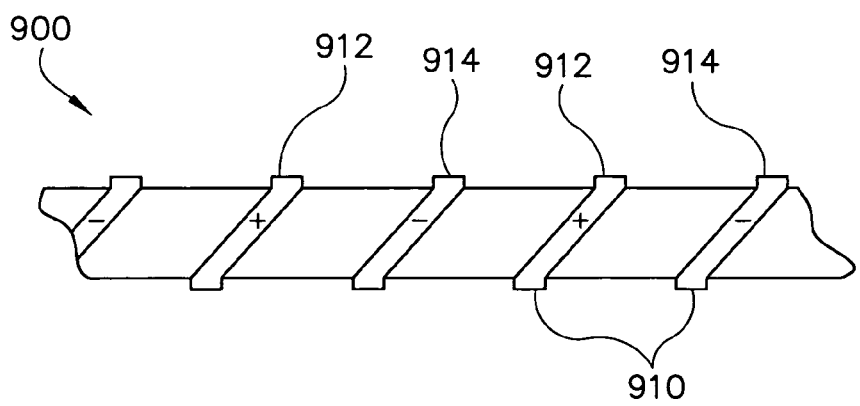
FIG. 10 is a fragmentary elevation of the fifth embodiment showing the coating removed.

FIG. 9 shows a fifth embodiment of a suture 900 according to the present invention in which a plurality of conductors 910 is helically disposed around the core 750. Although two conductors, designated by 912 and 914, are shown in FIG. 8, more than two conductors 910 may be used without departing from the scope of the present invention. The conductors 910 may carry the same or differing charges. For example, first and second conductors 912, 914 may carry opposite charges as shown in FIG. 10. When relative conductors carry opposite charges, those conductors are spaced from one another over their entire lengths. The suture 900 of the fifth embodiment is otherwise identical to the suture of the first embodiment, and therefore will not be described in further detail.

Although a preferred use of the fusible suture is to connect tissue during surgery, the suture may also be used to connect objects in non-surgical environments. In view of the above, it will be seen that the several objects of the invention are achieved.

When introducing elements of the present invention or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

What is claimed is:

1. A fusible suture for joining portions of tissue comprising:
   an elongate electrical conductor extending between opposite ends, said conductor having sufficient flexibility to permit segments of said conductor to overlap thereby forming a loop sized for joining portions of tissue, said overlapping segments of the conductor being heated upon application of an electrical current to the conductor; and
   a coating at least partially covering the conductor and extending over at least one of said segments of the conductor, said coating softening when its temperature is at and above a softening temperature so that the overlapping segments of the coating coalesce and returning to a non-softened state when its temperature falls below a hardening temperature thereby to form a bond between the overlapping segments of the conductor, said softening temperature being lower than a melting temperature of the conductor; and
   wherein the conductor includes an inner conductor portion having an outer surface, an outer conductor portion concentrically positioned outside the outer surface of the inner conductor portion, and a flexible jacket positioned between the inner and outer conductor portions.

2. A suture as set forth in claim 1 wherein the jacket comprises a carbon-based material and the coating extends over at least a portion of the outer conductor portion.

3. A suture as set forth in claim 1 wherein the jacket is less conductive than said inner and outer conductor portions.

4. A suture as set forth in claim 1 wherein the outer conductor portion is wound around the jacket.

5. A suture as set forth in claim 1 wherein the coating comprises an epoxy.

6. A suture as set forth in claim 1 wherein the conductor comprises a plurality of conductor portions.

7. A suture as set forth in claim 1 further comprising a core having an exterior surface, said conductor extending over at least a portion of the exterior surface of the core and being more conductive than the core.

8. A suture as set forth in claim 7 wherein the core comprises a carbon-based material.

9. A suture as set forth in claim 7 wherein the conductor is wound about the exterior surface of the core.

10. A suture as set forth in claim 9 wherein the conductor comprises a plurality of conductor portions, and at least two of said plurality of conductor portions are spaced from one another over their entire lengths.

11. A suture as set forth in claim 10 wherein said two conductor portions carry opposite electrical charges.

12. A fusible suture for joining portions of tissue comprising:
    an elongate electrical conductor extending between opposite ends, said conductor having sufficient flexibility to permit segments of said conductor to overlap thereby forming a loop sized for joining portions of tissue, said overlapping segments of the conductor being heated upon application of an electrical current to the conductor, wherein the conductor includes an inner conductor portion having an outer surface, an outer conductor portion positioned concentrically outside the outer surface of the inner conductor portion, and a flexible jacket positioned between the inner and outer conductor portions; and
    a coating at least partially covering the conductor and extending over at least one of said segments of the conductor, said coating softening when its temperature is at and above a softening temperature so that the overlapping segments of the coating coalesce and returning to a non-softened state when its temperature falls below a hardening temperature thereby to form a bond between the overlapping segments of the conductor, said softening temperature being lower than a melting temperature of the conductor.

* * * * *